US012453570B2

(12) United States Patent
Motoki et al.

(10) Patent No.: US 12,453,570 B2
(45) Date of Patent: Oct. 28, 2025

(54) SCISSORS FOR ENDOSCOPE

(71) Applicants: KABUSHIKI KAISHA FINETEC, Fukuoka (JP); Yorinobu Sumida, Yamaguchi (JP)

(72) Inventors: Hiroshi Motoki, Fukuoka (JP); Yorinobu Sumida, Yamaguchi (JP)

(73) Assignees: KABUSHIKI KAISHA FINETEC, Fukuoka (JP); Yorinobu Sumida, Yamaguchi (JP)

( * ) Notice: Subject to any disclaimer, the term of this patent is extended or adjusted under 35 U.S.C. 154(b) by 464 days.

(21) Appl. No.: 17/992,499

(22) Filed: Nov. 22, 2022

(65) Prior Publication Data

US 2023/0091456 A1 Mar. 23, 2023

Related U.S. Application Data

(63) Continuation of application No. PCT/JP2022/002026, filed on Jan. 20, 2022.

(30) Foreign Application Priority Data

Jan. 28, 2021 (JP) ................................ 2021-011581

(51) Int. Cl.

| | |
|---|---|
| ***A61B 18/14*** | (2006.01) |
| ***A61B 17/32*** | (2006.01) |
| ***A61B 17/3201*** | (2006.01) |

(52) U.S. Cl.

CPC .. *A61B 17/320016* (2013.01); *A61B 17/3201* (2013.01); *A61B 18/14* (2013.01); *A61B 2018/1415* (2013.01)

(58) Field of Classification Search

CPC ........ A61B 17/320016; A61B 17/3201; A61B 18/14; A61B 18/1442; A61B 2018/00982;

(Continued)

(56) References Cited

U.S. PATENT DOCUMENTS 5,827,281 A * 10/1998 Levin ................ A61B 18/1445 606/49
6,562,035 B1 * 5/2003 Levin ................ A61B 18/1442 606/45

(Continued)

FOREIGN PATENT DOCUMENTS

CN 111759459 * 10/2020
CN 111759459 A 10/2020

(Continued)

OTHER PUBLICATIONS

International Search Report issued in PCT/JP2022/002026 mailed on Apr. 12, 2022 with English Translation (5 pages).

(Continued)

*Primary Examiner* — Michael F Peffley

(74) *Attorney, Agent, or Firm* — Nakanishi IP Associates, LLC

(57) ABSTRACT

Provided are Scissors for an endoscope that include a scissor mechanism part that includes a pair of scissor members connected to each other by a first spindle, and cuts a target site by opening and closing of the one scissor member and the other scissor member with the first spindle as a fulcrum; and an electrode part in which a monopolar electrode (electrode part) is formed on a distal end part of the one scissor member of the one scissor member and the other scissor member. An operator can quickly and extensively cut the target site by using the scissor mechanism part by the pair of scissor members, or can stop bleeding at the target site or cut the target site by using the electrode part.

7 Claims, 7 Drawing Sheets

(58) Field of Classification Search
CPC .... A61B 2018/1415; A61B 2018/1417; A61B 2018/146
See application file for complete search history.

(56) References Cited

U.S. PATENT DOCUMENTS

| | | | | |
|---|---|---|---|---|
| 7,367,976 | B2 * | 5/2008 | Lawes | A61B 18/1445 606/41 |
| 7,972,333 | B2 * | 7/2011 | Nishimura | A61B 18/1442 606/50 |
| 8,105,320 | B2 * | 1/2012 | Manzo | A61B 17/3201 901/14 |
| 8,298,231 | B2 * | 10/2012 | Sartor | A61B 18/1442 606/51 |
| 8,475,455 | B2 * | 7/2013 | McClurken | A61B 18/1445 606/51 |
| 2005/0137590 | A1 | 6/2005 | Lawes et al. | |
| 2007/0044316 | A1 | 3/2007 | Bohlman et al. | |
| 2008/0243120 | A1 | 10/2008 | Lawes et al. | |
| 2009/0125027 | A1 | 5/2009 | Fischer | |
| 2011/0004209 | A1 | 1/2011 | Lawes et al. | |
| 2013/0023874 | A1 | 1/2013 | Lawes et al. | |
| 2014/0100569 | A1 | 4/2014 | Lawes et al. | |

FOREIGN PATENT DOCUMENTS

| | | | |
|---|---|---|---|
| JP | 2009-533109 | A | 9/2009 |
| JP | 2011-212449 | A | 10/2011 |

OTHER PUBLICATIONS

Written Opinion of International Searching Authority issued in PCT/JP2022/002026 mailed on Apr. 12, 2022 with English Translation (4 pages).

* cited by examiner (A)

(B)

SCISSORS FOR ENDOSCOPE

TECHNICAL FIELD

The present invention relates to scissors for an endoscope for poking out of a distal end of an insertion part of an endoscope and performing treatment.

BACKGROUND ART

As a device for an endoscope (treatment tool), various devices are prepared. There are known, for example, forceps that grip and press or pick up tissue, and scissors that cut tissue. In addition, a monopolar electrode type electric knife, bipolar electrode type forceps, and the like are known as devices that cut tissue and fuse tissue to stop bleeding by causing a high-frequency current to flow.

For example, Patent Literature 1 describes a multifunction device for endoscopic surgery with forceps or a clamp that is also formed as a jaw part capable of grasping and holding tissue as a bipolar electrode, and incorporates a circular disc-like monopolar electrode in a solid jaw part.

Further, Patent Literature 2 describes bipolar forceps including, in one of a pair of jaw members facing each other, a monopolar extension part housing a monopolar element selectively extending.

CITATION LIST

Patent Literature

Patent Literature 1: Japanese Translation of PCT International Application Publication No. 2009-533109

Patent Literature 2: Japanese Patent Laid-Open No. 2011-212449

SUMMARY OF INVENTION

Technical Problem

In the conventional forceps for an endoscope described in each of Patent Literatures 1 and 2, the monopolar electrode is thus provided in the forceps, and therefore it is possible to cut tissue with the monopolar electrode while gripping the tissue, or stop bleeding.

However, in a case where tissue is cut extensively and quickly, it is necessary to pull out the conventional forceps for an endoscope having the monopolar electrode from a port of an endoscope, and replace the scissors for the endoscope. Further, in a case where a target site to be cut is fibrotic tissue of little moisture content, it is difficult to cut the target site with a high-frequency current from the monopolar electrode, and it is required for replacement of the scissors for an endoscope similarly, and therefore treatment requires labor and time.

An object of the present invention is to provide scissors for an endoscope enabling reduction in labor during treatment and reduction in time required for the treatment.

Solution to Problem

Scissors for an endoscope of the present invention include: a scissor mechanism part that includes a pair of scissor members connected to each other by a spindle, and cuts a target site by opening and closing of the pair of scissor members with the spindle as a fulcrum; and an electrode part on which a monopolar electrode is formed on a distal end part of one scissor member of the pair of scissor members.

According to the scissors for an endoscope of the present invention, an operator can quickly and extensively cut the target site by using the scissor mechanism part by the pair of scissor members, or can stop bleeding at the target site or cut the target site by using the monopolar electrode. Therefore, it is possible to perform various treatments without replacement of the scissors for an endoscope of the present invention.

The electrode part can be formed at such a position that a center line of the scissor mechanism part, which passes through the spindle, and a center line along a protruding direction of the monopolar electrode coincide with each other when the pair of scissor members are closed.

Even when an insertion part of the endoscope is rotated around the axis, and the scissors for an endoscope of the present invention is rotated around the axis, the monopolar electrode is formed at such a position that the center line of the scissor mechanism part and the center line along the protruding direction of the monopolar electrode coincide with each other. Therefore, it is possible to prevent the direction of the monopolar electrode toward the target site from being displaced from the target site, and therefore the treatment can be performed in a stable state.

The electrode part can include a base that has the same thickness as a thickness of the one scissor member, and can be provided on a thickness surface of the one scissor member.

The one scissor member and the monopolar electrode can be formed from a single metal plate by punching, and the one scissor member and the monopolar electrode can be cut out integrally. Therefore, the manufacturing is easy.

The electrode part can be formed such that the distal end part has a shorter width direction thickness direction orthogonal to a thickness direction protruding direction while maintaining a thickness.

The distal end part of the monopolar electrode can be formed into a sharp shape, and therefore arc discharge can be reliably dissipated toward the target site from the distal end part, and the target site can be treated.

The electrode part can include a base formed of a rod-like body, and a block part formed on a distal end of the base. The block part is provided on the base formed of the rod-like body, so that the block part can be a semispherical body, a cylindrical body, a polygonal columnar body, a body with an elliptical cross section, a conical body, or the like.

The block part can be formed in a polygonal columnar shape. The block part is formed in a polygonal columnar shape, so that a high-frequency current is more concentrated when the distal end is sharp, and the arc discharge is more likely to dissipate. Therefore, the block part is formed in the polygonal shape, so that the arc discharge can dissipate from a corner closest to the tissue.

The block part can be formed in an octagonal columnar shape. When the block part is octagonal columnar, it is easy to aim, and it is easier to dissipate a high-frequency current to a desired site.

Another scissor member of the pair of scissor members can be a cutter having a blade part, and the one scissor member of the pair of scissor members can be a die having a first surface receiving the target site, and a second surface facing a flank face of the cutter when the cutter moves in a cutting direction.

Advantageous Effect of Invention

Scissors for an endoscope of the present invention can perform various treatments without replacement, and therefore it is possible to reduce labor during treatment and shorten time required for the treatment.

DESCRIPTION OF EMBODIMENTS

Scissors for an endoscope according to an embodiment of the present invention will be described with reference to the drawings.

In this specification, the description will be made while the scissors side is defined as the distal end side or the front side, and the wire side is defined as the proximal end side or the back side. In addition, the description will be made while the direction of pushing a wire to open the scissors is defined as the advancing direction, and the direction of pulling the wire to close the scissors is defined as the retreating direction.

Figure 1:
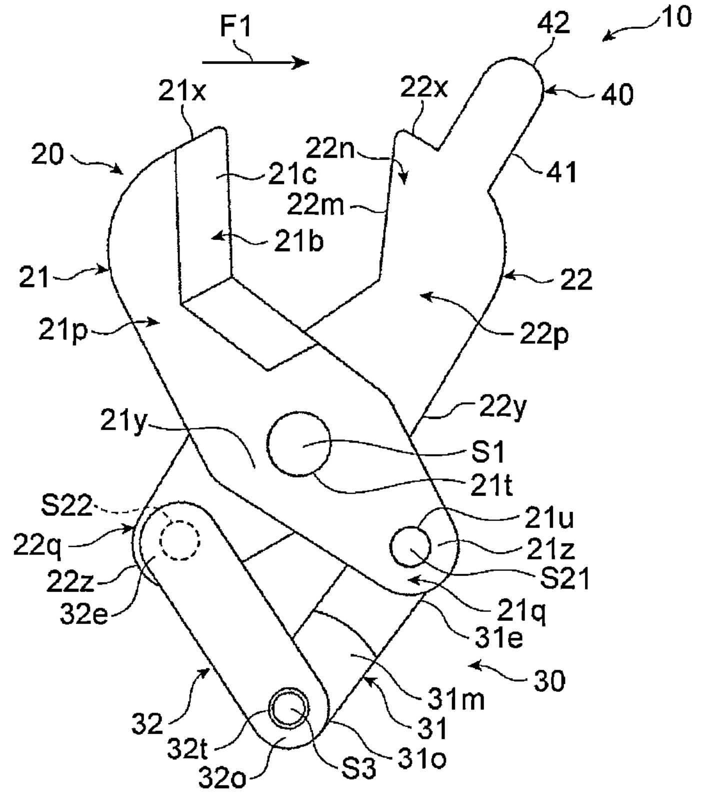
FIG. 1 is a diagram illustrating scissors for an endoscope according to an embodiment of the present invention, in which (A) of FIG. 1 is a diagram of a state in which a scissor mechanism part is open, and (B) of FIG. 1 is a diagram of a state in which the scissor mechanism part is closed.
Figure 1:
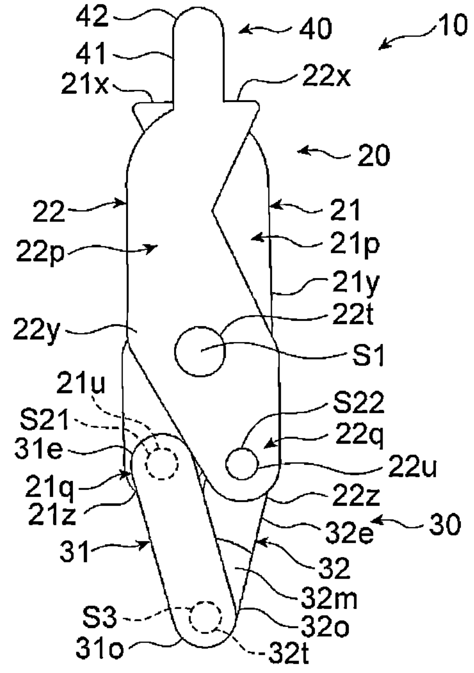

Scissors 10 for an endoscope illustrated in FIG. 1(A) and FIG. 1(B) are scissors that are inserted from a forceps port of the endoscope in a state in which a scissor mechanism part is closed, are poked out of a suction port of a distal end of an insertion part, and cut tissue which is a target site.

The scissors 10 for an endoscope includes a scissor mechanism part 20, a link mechanism part 30, and an electrode part 40. For example, the scissor mechanism part 20 according to this embodiment is formed such that the length from a proximal end part to a distal end part is about 6 mm. The scissor mechanism part 20 is formed so as to have a thickness of about 0.5 mm. The electrode part 40 is formed so as to have about 1.5 mm.

The scissor mechanism part 20 includes a pair of scissor members (one scissor member 22, the other scissor member 21), and a first spindle S1 (spindle) connecting the pair of scissor members 21 and 22 openably and closably, and is formed in an X-shape.

In the scissor member 21, a cut side 21*p* from a distal end part 21*x* to a central part 21*y* in which a through hole 21*t* is formed into which the first spindle S1 is inserted is formed in a substantially V-shape, and an operation side 21*q* from the central part 21*y* to a proximal end part 21*z* is formed so as to have a gradually narrowed width.

A through hole 21*u* for connecting the link mechanism part 30 and the scissor member 21 is formed in the proximal end part 21*z* of the scissor member 21.

Figure 4:
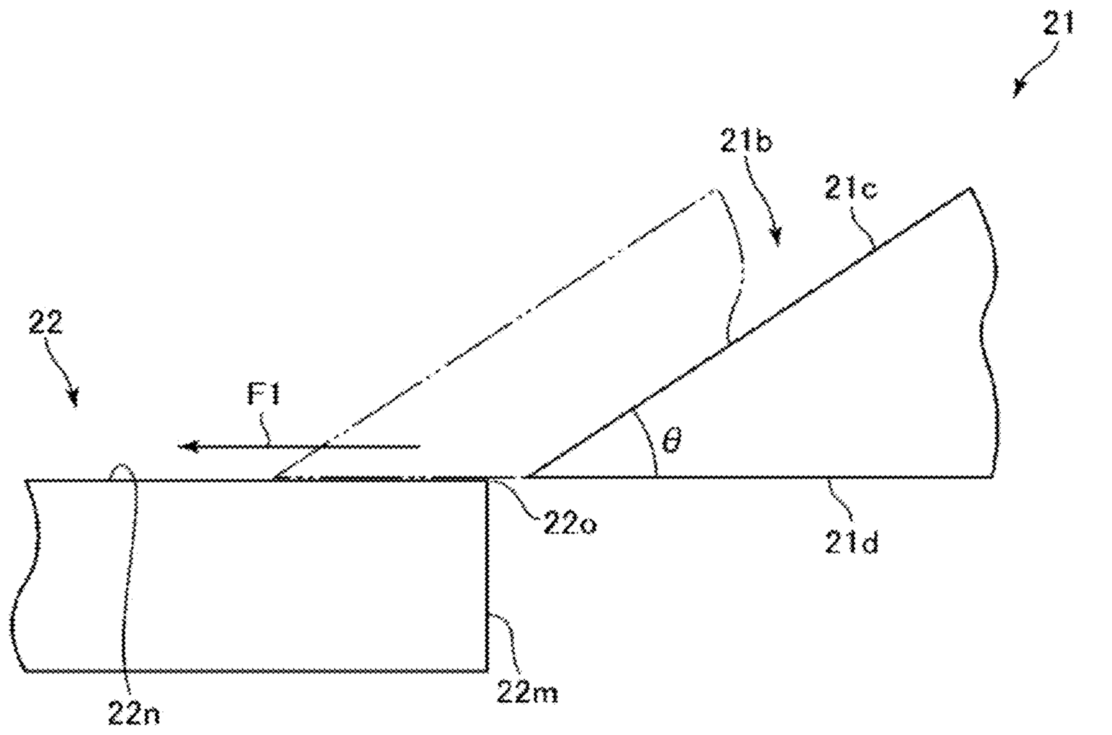
FIG. 4 is a schematic diagram illustrating a state in which a pair of scissor members of the scissors for an endoscope illustrated in FIG. 1 are overlapped on each other.

An inner surface of the cut side 21*p* of the scissor member 21 has a blade surface whose thickness gradually decreases formed therein, so that the scissor member 21 functions as a cutter having a blade part 21*b*. In this embodiment, as illustrated in FIG. 4, an angle θ (blade angle) between a rake face 21*c* inclined with respect to the cutting direction F1 (closing direction) of the scissor member 21 and a flank face 21*d* parallel to the cutting direction F1 is formed to have 20° to 40°.

Figure 2:
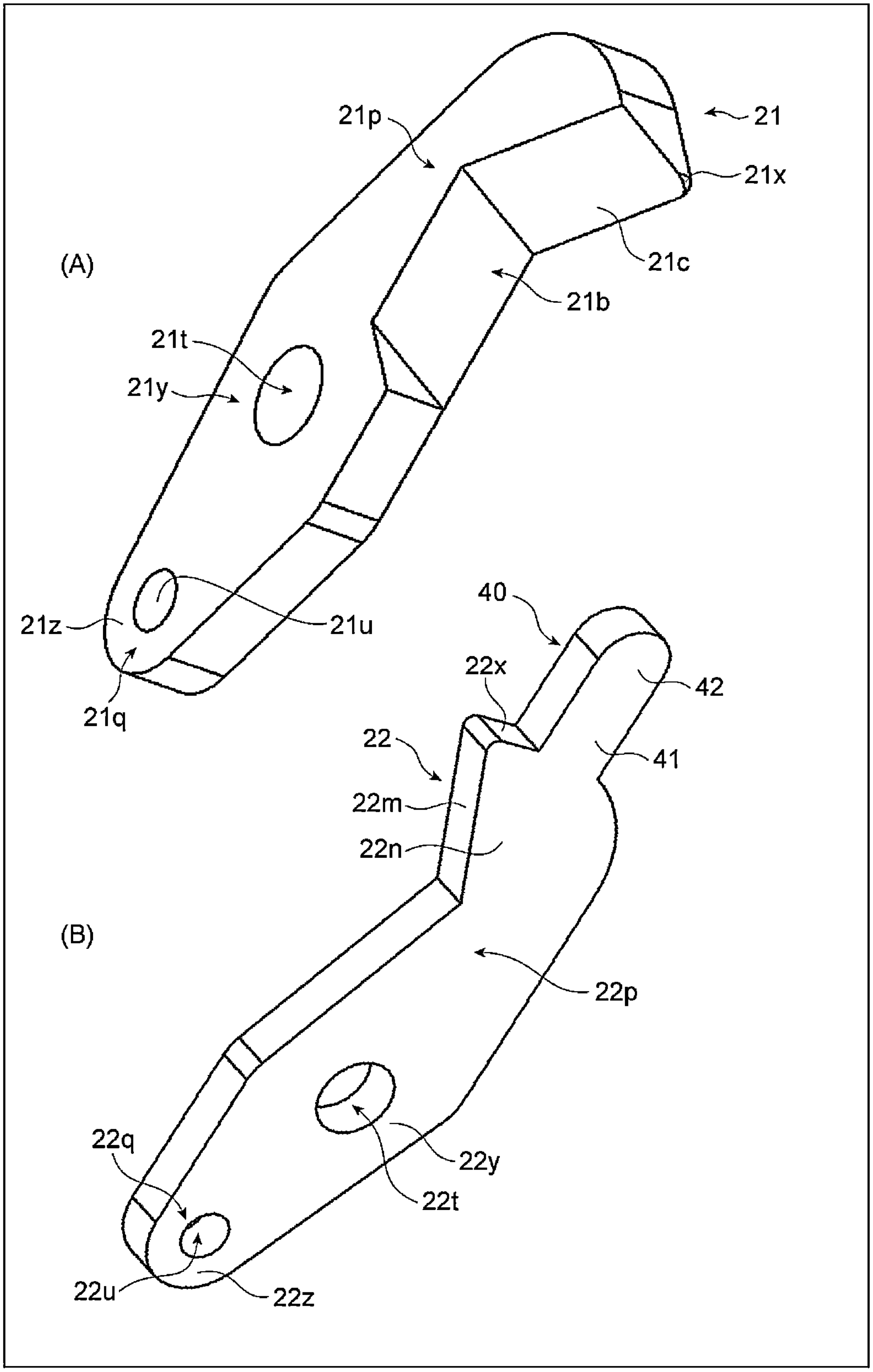
FIG. 2 is a diagram of the scissor mechanism part of the scissors for an endoscope illustrated in FIG. 1, in which (A) of FIG. 2 is a diagram of a scissor member formed in a cutter, and (B) of FIG. 2 is a diagram of a scissor member formed in a die.

In the one scissor members 22 illustrated in FIG. 1(A), FIG. 1(B), and FIG. 2(B), similarly to the scissor member 21, a cut side 22*p* from a distal end part 22*x* to a central part 22*y* in which a through hole 22*t* is formed into which the first spindle S1 is inserted is formed in a substantially V-shape, and an operation side 22*q* from the central part 22*y* to a proximal end part 22*z* is formed so as to have a gradually narrowed width.

A through hole 22*u* for connecting the link mechanism part 30 and the scissor member 22 is formed in the proximal end part 22*z* of the scissor member 22.

An inner surface of the cut side 22*p* of the scissor member 22 functions as a die having a first surface 22*m* that receives a target site, and a second surface 22*n* facing the flank face 21*d* (see FIG. 4) of the scissor member 21 when the scissor member 21 functioning as a cutter moves in the cutting direction F1 (closing direction).

In this embodiment, the second surface 22*n* is a surface parallel to the cutting direction F1.

The scissor members 21 and 22 are formed to have the same length from the through holes 21*t* and 22*t* into which the first spindle S1 of the scissor members 21 and 22 is inserted to the through holes 21*u* and 22*u* into which a second spindle described below is inserted.

As illustrated in FIG. 1(A) and FIG. 1(B), in the link mechanism part 30, a pair of links 31 and 32 having the same length are connected to the proximal end parts 21*z* and 22*z* of the scissor mechanism part 20 by a pair of second spindles S21 and S22, respectively.

The second spindle S21 integrally formed in a first end 31*e* of the link 31 is rotatably inserted into and fixed to the through hole 21*u* (see FIG. 2(A)) of the scissor member 21, so that the one link 31 and the scissor member 21 are connected.

The second spindle S22 integrally formed in a first end 32*e* of the link 32 is rotatably inserted into and fixed to the through hole 22*u* (see FIG. 2(B)) of the scissor member 22, so that the other link 32 and the scissor member 22 are connected.

A third spindle S3 is integrally formed with the link 31 in a second end 31*o* of the link 31. A through hole 32*t* into which the third spindle S3 is inserted is formed in a second end 32*o* of the link 32 in order to connect a wire (not illustrated) together in a state in which the second ends 31*o* and 32*o* are overlapped on each other.

Further, thin wall parts 31*m* and 32*m* are formed in the second ends 31*o* and 32*o* of the links 31 and 32, respectively, such that even when a connecting part for connecting the wire is disposed between the second ends 31*o* and 32*o*, the overlapped thickness of the links 31 and 32 is not changed.

The third spindle S3 is formed at such a length as to protrude from the link 32.

Figure 3:
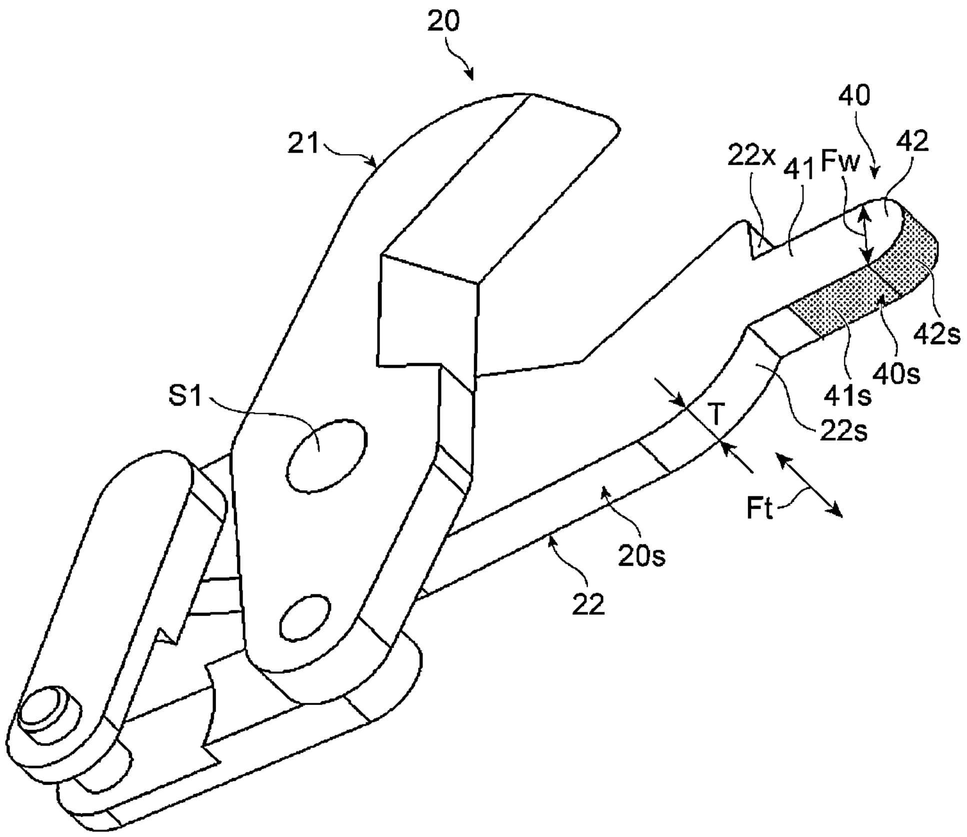
FIG. 3 is a diagram for illustrating an electrode part of the scissors for an endoscope illustrated in FIG. 1, and illustrates an exposed surface and an insulating surface.
Figure 5:
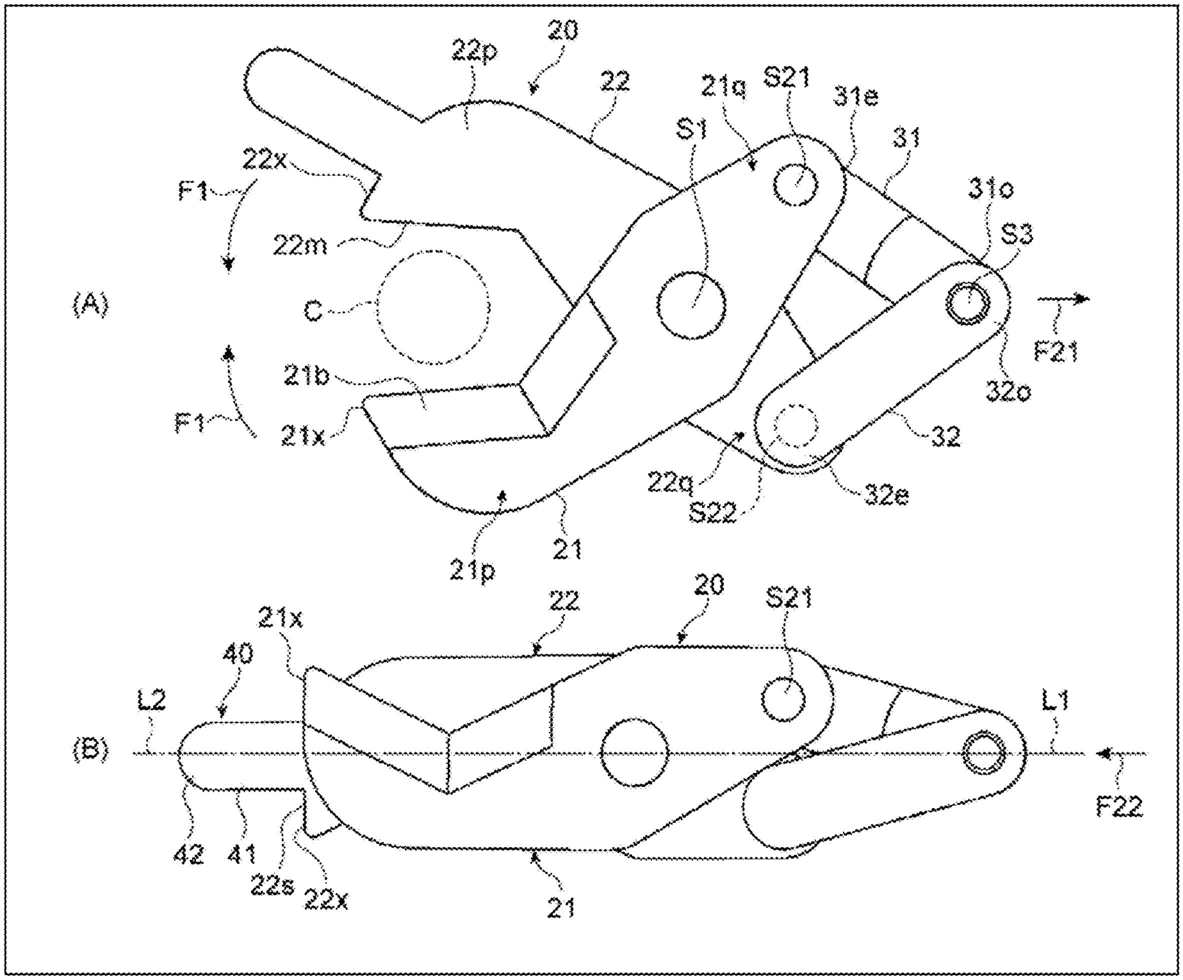
FIG. 5 is a schematic diagram illustrating opening/closing operation of the scissors for an endoscope illustrated in FIG. 1, in which (A) of FIG. 5 is a diagram of a state in which scissor members are open, and (B) of FIG. 5 is a diagram of a state in which the scissor members are closed.

As illustrated in FIG. 3, the electrode part 40 has the same thickness as the thickness T of the scissor member 22, and is a monopolar electrode formed by a rod-like member protruding from a thickness surface 22*s* of the distal end part 22*x* of the scissor member 22. As illustrated in FIG. 5(B), the electrode part 40 is formed at such a position that a center line L1 of the scissor mechanism part 20, which passes through the first spindle S1, and a center line L2 along the protruding direction of the electrode part 40 coincide with each other when the scissor members 21 and 22 (scissor mechanism part 20) are closed.

As illustrated in FIG. 3, the electrode part 40 includes a square rod-like base 41, and a semi-circular distal end part 42 extending from a tip of the base 41. The electrode part 40 is formed such that the distal end part 42 has a semicircle while maintaining the thickness. Accordingly, the electrode part 40 is formed such that while the distal end part 42 maintains the thickness, the width direction Fw orthogonal to the thickness direction Ft is shortened.

The electrode part 40 is formed on a discharge surface 40*s* where a part of a thickness surface 41*s* on the distal end part 42 side in the base 41 and a thickness surface 42*s* of the distal end part 42 are exposed from an insulating film. Accordingly, a surface of the scissors 10 for an endoscope other than the discharge surface 40*s* of the electrode part 40 is formed on an insulating surface 20*s* covered with the insulating film.

A use state of the thus configured scissors for an endoscope according to the embodiment of the present invention will be described with reference to the drawings.

As illustrated in FIG. 5(A), a target site C is placed between the scissor members 21 and 22 of the scissor mechanism part 20 which is open. An operator pulls the wire (not illustrated) connected to the spindle S3 in the retreating direction F21, so that the second ends 31*o* and 32*o* of the links 31 and 32 connected to the third spindle S3 move backward (in the retreating direction F21). The second ends 31*o* and 32*o* of links 31 and 32 move backward, so that the first ends 31*e* and 32*e* are pulled backward.

Thus, the operation sides 21*q* and 22*q* of the scissor members 21 and 22 connected to the first ends 31*e* and 32*e* of the links 31 and 32 by the second spindles S21 and S22 move in the closing direction with the first spindle S1 as a fulcrum. With the movement of the operation sides 21*q* and 22*q* in the closing direction, the sides of the cut sides 21*p* and 22*p* of the scissor members 21 and 22 move in the closing direction.

At this time, as illustrated in FIG. 4, the blade part 21*b* of the scissor member 21 and the first surface 22*m* (facing surface) of the scissor member 22 come into contact with the target site located in a range surrounded by the scissor members 21 and 22.

The target site that comes into contact with the scissor member 21 having the blade part 21*b* may start being cut at that point. In addition, the target site that comes into contact with a right-angled shoulder 22*o* formed by the first surface 22*m* and the second surface 22*n* of the scissor member 22 may also start being cut.

However, in many cases, an interval between the distal end parts of the cut sides 21*p* and 22*p* in the scissor members 21 and 22 becomes narrower, so that even when a target site such as a viscoelastic wall part or a fibrous and hard wall part comes into contact with the scissor members 21 and 22, the target site may slide on the blade part 21*b* and the first surface 22*m*, and escape while shifting. Further, an interval between the proximal end parts of the cut sides 21*p* and 22*p* becomes narrower, so that the target site may escape while shifting.

As illustrated in FIG. 5(A), the blade part 21*b* of the scissor member 21 and the first surface 22*m* which is a receiving surface of the scissor member 22 are formed in a recessed V-shape.

Therefore, when the target site C is sandwiched between the distal end sides of the cut sides 21*p* and 22*p* in the scissor members 21 and 22, the target site C can be cut on the distal end side. Further, even when the target site C escapes while shifting on the distal end side, the target site C can be moved to the central sides of the blade part 21*b* and the first surface 22*m* as the scissor members 21 and 22 close.

When the target site C is sandwiched between the proximal end sides of the cut sides 21*p* and 22*p* in the scissor members 21 and 22, the target site C can be cut on the proximal end side. Even when the target site C escapes while sliding on the proximal end, the target site C can be moved on the central sides of the blade part 21*b* and the first surface 22*m* as the scissor members 21 and 22 close.

As illustrated in FIG. 5(B), the scissor members 21 and 22 are overlapped by further pulling of the wire, and the scissor members 21 and 22 are closed, so that the target site C is cut from such a position that both the distal end and proximal end sides of the scissor members 21 and 22 are overlapped.

Accordingly, the scissor members 21 and 22 can cut from both the distal end and proximal end sides of the cut sides 21*p* and 22*p*, and therefore even a wall part has elasticity and is likely to slide due to a mucous membrane or the like, the target site C can be cut without allowing the target to escape.

The blade part 21*b* is formed up to the distal end part 21*x* (blade edge) of the scissor member 21, and is sharp. Therefore, even when the wall part is located at the distal end part 21*x*, the distal end part 21*x* can bite into the wall part to be contacted and press the wall part against the first surface 22*m* of the scissor member 22. Accordingly, the wall part can be placed between the scissor members 21 and 22 and be cut without allowing the wall part to escape.

Thus, the blade part 21*b* by the rake face 21*c* and the flank face 21*d* is formed, so that the scissor member 21 functions as a cutter, and the scissor member 22 functions as a die having the first surface 22*m* and the second surface 22*n*.

For example, when the scissors includes the blade parts that are made by cutters formed in both scissor members, biting to the target site is improved, and excellent sharpness is obtained. However, the thickness of the blade edge (blade width) is thin and linear, and therefore it is difficult to secure high strength.

However, in the scissors 10 for an endoscope according to this embodiment, while the scissor members in the scissor mechanism part 20 securely receive and hold a wall part of a target site by the first surface 22*m* of the scissor member 22 illustrated in FIG. 4, the blade part 21*b* of the scissor member 21 sandwiches and cuts the wall part, and passes by the second surface 22*n* of the scissor member 22 as it is. Therefore, the thickness of the blade edge (blade width) is thick and planar, and therefore the strength is high, and the blade part 21*b* of the scissor member 21 is not chipped or cracked.

Accordingly, the scissors 10 for an endoscope according to this embodiment can be excellent in sharpness, and be resistant to chipping and cracking of the blade part.

When both the scissor members are cutters, a sharp blade part needs to be formed on both the scissor members, which takes time to process. However, in the scissors 10 for an endoscope according to this embodiment, the scissor member 22 is formed as a die, and therefore it is possible to shorten processing time compared to a case where the scissor member 22 is formed as a cutter.

When the scissor members 21 and 22 are open again, the wire (not illustrated) is pushed in the advancing direction F22 as illustrated in FIG. 5(B), so that the distal end parts 21*x* and 22*x* (cut sides 21*p* and 22*p*) of the scissor members 21 and 22 illustrated in FIG. 5(A) are open by operation opposite to the above description.

When bleeding occurs due to incision in a tissue serving as a target site, hemostasis is required. An operator points the electrode part 40 toward a portion requiring the hemostasis while keeping the scissor mechanism part 20 illustrated in FIG. 5(B) closed.

Then, a control device (not illustrated) is operated, and a high-frequency current adjusted for the hemostasis is output to the electrode part 40. The high-frequency current flows as arc discharge from the discharge surface 40*s* (see FIG. 3) of the electrode part 40, which is not coated with the insulating film, to the tissue at the treatment site, so that the target site is coagulated and bleeding at the target site is stopped.

When the tissue is cut, the operator operates the control device, and a high-frequency current adjusted for the cutting is output to the electrode part 40. Similarly to the case of hemostasis, the high-frequency current flows as arc discharge from the discharge surface 40*s* of the electrode part 40 to the tissue at the treatment site, so that the target site is burned off and separated.

Thus, the operator can quickly and extensively cut the target site by using the scissor mechanism part 20 of the scissors 10 for an endoscope, or can stop bleeding at the target site or cut the target site by using the electrode part 40 of the monopolar electrode. In addition, even when the target site that is fibrotic tissue is not able to be incised by applying arc discharge from electrode part 40, the fibrotic tissue can be cut as it is by the scissor mechanism part 20 without replacement of the scissors 10 for an endoscope.

Accordingly, various treatments can be performed without replacement of the scissors 10 for an endoscope, and therefore the scissors 10 for an endoscope enables reduction in labor during treatment and reduction in time required for the treatment.

At this time, even in a case where the insertion part of the endoscope is rotated around the axis, and the scissors 10 for an endoscope is rotated around the axis, when the pair of scissor members 21 and 22 are closed as illustrated in FIG. 5(B), the electrode part 40 is formed at such a position that the center line L1 of the scissor mechanism part 20 and the center line L2 of the electrode part 40 coincide (thickness surface 22*s* of the distal end part 22*x*). Therefore, it is possible to prevent the direction of the electrode part 40 toward the target site from being displaced, and the treatment can be performed in a stable state.

As illustrated in FIG. 3, the electrode part 40 has the same thickness as the thickness T of the scissor member 22, and protrudes from the thickness surface 22*s* of the distal end part 22*x* of the scissor member 22, so that the scissor member 22 formed by a die and the electrode part 40 can be formed from a single metal plate by punching, and the scissor member 22 and the electrode part 40 can be cut out integrally. Therefore, the scissor member 22 and the electrode part 40 are easily manufactured.

The electrode part 40 is formed such that the distal end part 42 has a shorter width direction Fw orthogonal to the thickness direction Ft while maintaining the thickness. Therefore, it is possible to make it easier to dissipate the arc discharge from the discharge surface 40*s* (thickness surface 42*s*) of the distal end part 42 toward the target site, not from other portion of the electrode part 40, and it is possible to perform treatment on the target site.

When the distal end parts 21*x* and 22*x* of the scissor members 21 and 22 in the scissor mechanism part 20 are directed upward as illustrated in FIG. 1(A), and the scissor members 21 and 22 are opened left and right, and then as illustrated in FIG. 1(B), the state in which the scissor members 21 and 22 are closed and overlapped is viewed from the front, the distal end part 22*x* of the scissor member 22 extends to the right from a root of the electrode part 40, and the distal end part 21*x* of the scissor member 21 extends to the left from the root of electrode part 40, so that the distal end parts 21*x* and 22*x* extend in both the left and right directions around the electrode part 40.

Therefore, when the electrode part 40 is pushed into the target site and disconnected, the distal end parts 21*x* and 22*x* of the scissor members 21 and 22 function as a stopper by coming into contact with a peripheral part of the target site. Thus, the distal end part 22*x* of the scissor member 22 extends beyond the position of the electrode part 40, and the distal end part 21*x* of the scissor member 21 extends beyond the position of the electrode part 40, so that the distal end parts 21*x* and 22*x* extend in the both directions around the electrode part 40. Consequently, it is possible to prevent the electrode part 40 from entering too much. The electrode part 40 is prevented from penetrating deeply into the target site, and therefore it is less likely to cause perforation and safety can be improved.

In the scissor mechanism part 20, the scissor member 21 is formed as a cutter, and the scissor member 22 is formed as a die, so that when the scissor member 21 and the scissor member 22 are overlapped on each other, the tissue as the target site can be cut out by cutting, not shearing, and therefore it is possible to obtain excellent sharpness.

In this embodiment, the electrode part 40 is formed by providing the semi-circular distal end part 42 in the square rod-like base 41 with the thickness T of the scissor member 22. However, the electrode part can be provided with a conical part, a sphere part, a triangular pyramid part, a disk part, or a polygonal columnar block part at the distal end part of the rod-like member.

Figure 6:
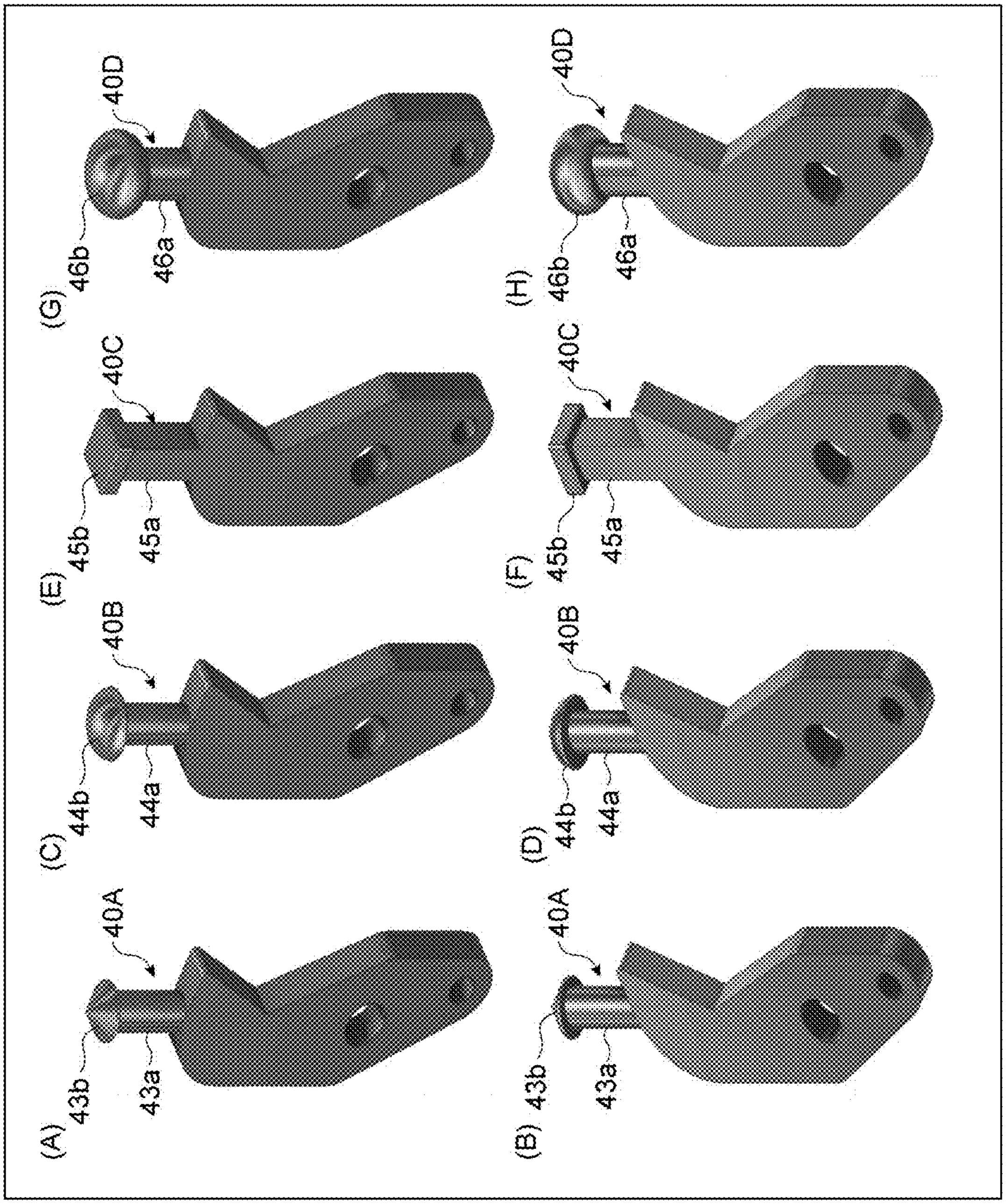
FIG. 6 shows diagrams (A)-(H) each illustrating a modification of an electrode part.

For example, an electrode part 40A illustrated in FIG. 6(A) and FIG. 6(B) includes a cylindrical rod-like member 43*a* and a conical block part 43*b*. An electrode part 40B illustrated in FIG. 6(C) and FIG. 6(D) includes a cylindrical rod-like member 44*a* and a semispherical block part 44*b*. An electrode part 40C illustrated in FIG. 6(E) and FIG. 6(F) includes a square columnar rod-like member 45*a* and a square plate-shaped block part 45*b*. An electrode part 40D illustrated in FIG. 6(G) and FIG. 6(H) includes a rod-like member 46*a* with an elliptical cross section and a spherical block part 46*b*.

Figure 7:
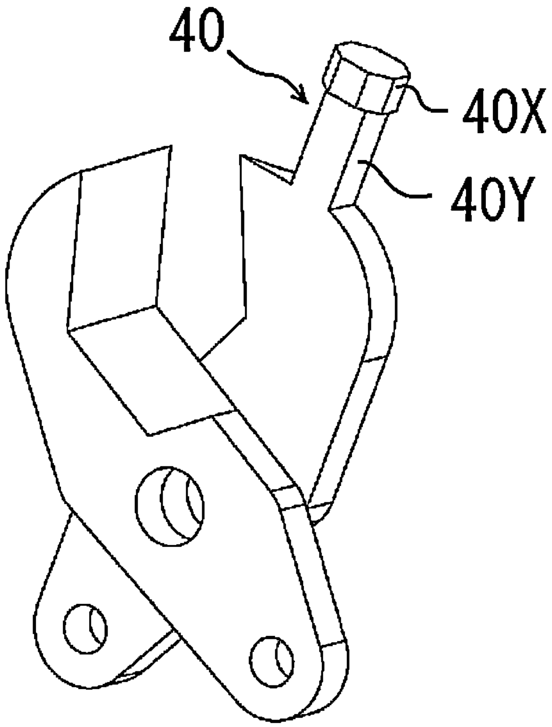
FIG. 7 is a diagram of a state in which an octagonal columnar block part is provided in a rod-like member of an electrode part.

As illustrated in FIG. 7, the electrode part 40 can be provided with an octagonal columnar block part 40X at a distal end of a rod-like member 40Y.

A high-frequency current is more concentrated when the distal end is sharp, and the arc discharge is more likely to dissipate. For example, in the case of a square columnar (rectangular parallelopiped or cubic) block part, the square columnar block part has four corners on a top surface, but in the case of the octagonal columnar block part 40X, the octagonal columnar block part has eight corners. Therefore, the octagonal columnar block part can locate the eight corners closest to the tissue, and the arc discharge can be likely to dissipate from any of the eight corners. Therefore, the octagonal columnar shape is easier to aim than the square columnar shape, and it is easier to dissipate a high-frequency current to a desired site.

However, when the polygonal shape has more corners than the octagonal columnar shape, the internal angle is larger than 135° of an octagon, and therefore the corners become obtuse, so that the arc discharge is unlikely to dissipate.

Therefore, it is desirable that the block part 40X of the distal end of the electrode part 40 is octagonal columnar.

Thus, the block parts 43*b* to 46*b* illustrated in FIG. 6(A) to FIG. 6(H), and the block part 40X illustrated in FIG. 7 are formed so as to protrude from respective upper end surfaces of the rod-like members 43*a* to 46*a* and 40Y toward the periphery with the axes as the centers, so that it is possible to cut while hooking the peripheral edge of each of the protruded block parts 43*b* to 46*b* and 40X to the target site.

The scissor mechanism part 20 of this embodiment is composed of a combination of the scissor member 21 that functions as a cutter and the scissor member 22 that functions as a die. However, as illustrated in FIG. 7, the scissor member may be a combination of a cutter and a cutter, or may be a combination of a die and a die (not illustrated).

INDUSTRIAL APPLICABILITY

The present invention is suitable for scissors for an endoscope for poking out of a distal end of an insertion part of an endoscope and performing treatment.

REFERENCE SIGNS LIST

10 scissors for endoscope
20 scissor mechanism part
20*s* insulating surface
21, 22 scissor member
21*b* blade part
21*c* rake face
21*d* flank face
22*m* first surface
22*n* second surface
22*o* shoulder
22*s* thickness surface
21*p*, 22*p* cut side
21*q*, 22*q* operation side
21*t*, 21*u*, 22*t*, 22*u* through hole
21*x*, 22*x* distal end part
21*y*, 22*y* central part
21*z*, 22*z* proximal end part
30 link mechanism part
31, 32 link
31*e*, 32*e* first end
31*o*, 32*o* second end
31*m*, 32*m* thin wall part
32*t* through hole
40, 40A to 40D electrode part
40*s* discharge surface
41 base
42 distal end part
41*s*, 42*s* thickness surface
43*a* to 46*a* rod-like member
43*b* to 46*b* block part
40X block part
40Y rod-like member
S1 first spindle
S21, S22 second spindle
S3 third spindle
L1 center line of scissor mechanism part
L2 center line of electrode part
F1 cutting direction
F21 retreating direction
F22 advancing direction
Ft thickness direction
Fw width direction
θ angle
C target site

The invention claimed is:

1. Scissors for an endoscope comprising:
a scissor mechanism part that includes a pair of scissor members connected to each other by a spindle, and cuts a target site by opening and closing of the pair of scissor members with the spindle as a fulcrum; and
an electrode part in which a monopolar electrode is formed on a distal end part of only one scissor member of the pair of scissor members,
wherein the monopolar electrode protrudes from the distal end part of the one scissor member, without overlapping with another one of the pair of scissor members, in a state that the pair of the scissor members are closed, such that the monopolar electrode is capable of cutting the target site and stopping bleeding at the target site;
wherein the electrode part is formed at such a position that a center line of the scissor mechanism part, which passes through the spindle, and a center line along a protruding direction of the monopolar electrode coincide with each other, in the state that the pair of scissor members are closed; and
wherein the electrode part, in entirety except a discharge surface thereof, is covered with an insulating film.

2. The scissors for an endoscope according to claim 1, wherein the electrode part includes a base that has the same thickness as a thickness of the one scissor member, and is provided on a thickness surface of the one scissor member.

3. The scissors for an endoscope according to claim 2, wherein the electrode part is formed such that the distal end part has a shorter width direction orthogonal to a thickness direction while maintaining a thickness.

4. The scissors for an endoscope according to claim 1, wherein the electrode part includes a base formed of a rod-like body, and a block part formed on a distal end of the base.

5. The scissors for an endoscope according to claim 4, wherein the block part is formed in a polygonal columnar shape.

6. The scissors for an endoscope according to claim 5, wherein the block part is formed in an octagonal columnar shape.

7. The scissors for an endoscope according to claim 1, wherein another scissor member of the pair of scissor members is a cutter having a blade part, and the one scissor member of the pair of scissor members is a die having a first surface receiving the target site, and a second surface facing a flank face of the cutter when the cutter moves in a cutting direction.

* * * * *